US00PP15775P3

(12) United States Plant Patent
Hatano

(10) Patent No.: US PP15,775 P3
(45) Date of Patent: May 24, 2005

(54) *ASTER TATARICUS* PLANT NAMED 'BLUE LAKE'

(50) Latin Name: *Aster tataricus*
Varietal Denomination: Blue Lake

(75) Inventor: Shoji Hatano, Yamanashi (JP)

(73) Assignee: Miyoshi & Co. Ltd., Tokyo (JP)

( * ) Notice: Subject to any disclaimer, the term of this patent is extended or adjusted under 35 U.S.C. 154(b) by 180 days.

(21) Appl. No.: 10/357,937

(22) Filed: Feb. 3, 2003

(65) Prior Publication Data

US 2004/0154066 P1 Aug. 5, 2004

(51) Int. Cl.[7] ..... A01H 5/00

(52) U.S. Cl. ..... Plt./355

(58) Field of Search ..... Plt./355

*Primary Examiner*—Anne Marie Grunberg

(74) *Attorney, Agent, or Firm*—Christie, Parker & Hale, LLP

(57) ABSTRACT

A new plant variety of *Aster tataricus* characterized by its late spring to early summer bloom season, a distinct blue cast of its ray flowers and its compactness, reaching a mature height of 2 to 3 feet tall.

1 Drawing Sheet

BACKGROUND OF THE INVENTION

Figure 1:
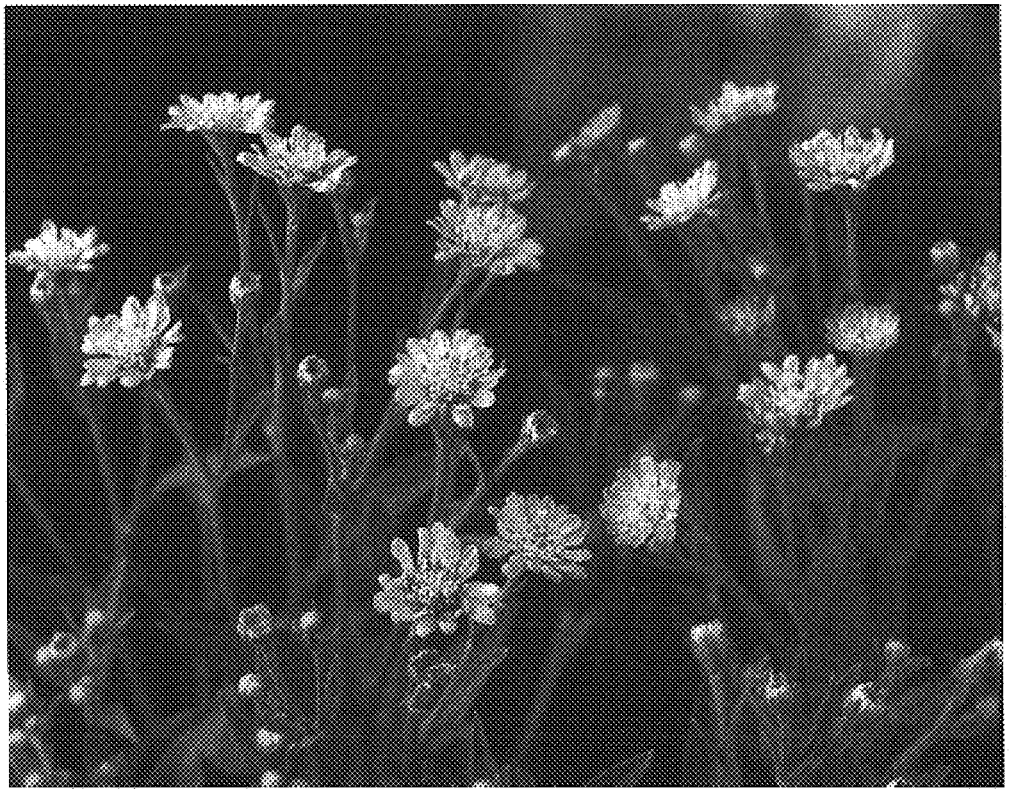

The present invention relates to a new and distinct variety of *Aster tataricus* L. f., which was developed in a controlled breeding program in Kitakoma-gun, Yamanashi, Japan by Mr. Shoji Hatano. The varietal denomination of the new variety is 'Blue Lake'.

The genus *Aster* is included in the family Compositae which comprises about 1,300 genera and 21,000 species of herbs, sometimes shrubs, or occasionally trees in tropics, mostly temperate in origin. *Aster* comprises approximately 250 species of mainly herbaceous perennials, though some annuals and biennials, originating in South America, Eurasia, Africa and Asia, many of which possess desirable ornamental characteristics.

*Aster tataricus* is is a rhizomatus perennial native to Japan, Korea, Manchuria, northern China, Mongolia and Siberia.

SUMMARY OF THE INVENTION

The new variety was discovered in a controlled breeding program and differs from its parent by its late spring to early summer bloom season, the distinct blue cast of its ray flowers and its compactness, reaching a mature height of 2 to 3 feet tall. Asexual reproduction of the new variety by division and flower stem cuttings, performed in Fulshear, Tex., have confirmed that the distinctive characteristics of the new variety are stable and transmitted to succeeding generations, and the new variety reproduces true to type.

COMPARISON WITH PARENTS

'Blue Lake' is distinguished from its parent and all other varieties of *Aster tataricus* of which I am aware by its late spring to early summer bloom season, the distinct blue cast of its ray flowers and its compactness, reaching a mature height of 2 to 3 feet tall.

BRIEF DESCRIPTION OF ILLUSTRATIONS

The accompanying illustrations show a specimen of the new cultivar in a photo illustration as true to color as is reasonably possible to make in an illustration of this character.

FIG. 1 illustrates the typical flower color of 'Blue Lake'.

DETAILED DESCRIPTION OF THE NEW VARIETY

'Blue Lake' has not been observed under all possible environmental, cultural and light conditions. The following observations and descriptions are of plants grown in Fulshear, Tex. In this description, color references are to The Royal Horticultural Society Colour Chart (1995) and terminology used in the color descriptions herein refers to plate numbers in this color chart. Phenotypic expression may vary with light intensity, cultural and environmental conditions.

CLASSIFICATION:

*Botanical.*—*Aster tataricus* L. f. 'Blue Lake'.

*Propagation.*—Division and flower stem cuttings.

*Time to rooting.*—Spring: about 21 days at a temperature of 21° C. winter: about 28 days at a temperature of 18° C.

*Rooting habit.*—Fine, fibrous, well-branched.

Plant description:

*Appearance.*—Herbaceous perennial with mounded growth habit with upright flower stems. Freely and uniformly flowering; violet-colored inflorescences.

*Size.*—Height: In flower, 50–60 cm; vegetative stage, 15–20 cm Width: 30–40 cm.

*Habit.*—Mounding.

*Branching.*—Leaves radiate from a stout caudex at or below the soil surface.

*Hardiness.*—USDA Zone 4 (−30° F. to −20° F.).

*Growth rate.*—Slow to moderate.

Foliage description:

*Shape.*—Oblanceolate.

*Apex.*—Acute.

*Base.*—Attenuate.

*Margin.*—Dentate.

*Leaf size.*—Mature: Width 6–8 cm, length 15–20 cm . Juvenile: Width 2–3 cm, length 6–7 cm.

*Arrangement.*—Whorl.

*Texture substance.*—Pubescent on upper and lower surface.

*Color.*—The following Color Readings are of mature specimens grown in Fulshear, Tex. Young foliage: Upper surface near Yellow-Green Group 146A. Under surface near Yellow-Green Group 147C. Mature Foliage: Upper side: Near Yellow-Green Group 147A . Under side: Near Green Group 137B.

*Venation.*—Pattern: Upper Surface: Pinnate. Under surface: Pinnate. Coloration: New Foliage: Upper Surface: near yellow-green 148B. Under Surface: Near Yellow-Green 146B. Mature Foliage: Upper Surface: near Yellow-Green 148C. Under Surface: Near Yellow-Green 146D.

Flowering description:

*Appearance.*—Daisy inflorescence form. Inflorescences held on stiff peduncles, arising from leaf axils; inflorescences face upright. Disc and ray florets developed acropetally on a capitulum.

*Flowering response.*—Under natural conditions, plants flower from spring through fall.

*Quantity of inflorescences.*—Inflorescences form at every leaf axil. Freely flowering, usually about 65–80 inflorescences per plant.

*Inflorescence size.*—Diameter: about 3 cm . Depth (height): About 1 cm . Disc diameter: About 8 mm.

*Fragrance.*—None.

*Inflorescence bud.*—Shape: Ovoid. Length: About 1 cm. Diameter: About 5 cm. Color: Near Green Group 138A.

*Ray florets.*—Quantity of ray florets/inflorescence: About 14–16 per inflorescence. Shape: Elliptic. Apex: Rounded. Base: Attenuate. Margin: Entire. Length: About 1.2–1.6 cm. Width: About 4–6 mm. Texture: Satiny, smooth and glabrous. Color: When opening, upper surface: Near Violet-Blue 91A. When opening, lower surface: Near Violet-Blue 92B. Mature, upper surface: Near violet Group 85D. Mature, lower surface: Violet-Blue Group 97D.

*Disc florets.*—Quantity: About 35–40 per inflorescence. Shape: Tubular. Length: About 6 mm. Width: About 2 mm. Color: Immature: Near Yellow Group 9B. Mature: Near Yellow Group 7C.

*Sepals.*—Appearance: Leaf-like. Quantity: Several rows. Shape: Linear. Texture: Smooth. Color: Near Green Group 139C.

*Peduncle.*—Aspect: Angled about 45°. Strength: Strong. Length: Apical peduncle: About 2 cm. Fourth peduncle: About 5 cm. Seventh peduncle: About 6 cm. Texture: Coarse. Color: Near Green Group 138B.

REPRODUCTIVE ORGANS

Androecium: Present on disc florets only.

*Pollen.*—Scarce.

*Pollen color.*—Near Yellow Group 9B.

Gynoecium: Present on both ray and disc florets.

*Style length.*—About 3 mm.

*Stigma color.*—Near Yellow Group 10C.

Seed production: Seed production has not been observed.

Disease resistance: Plants of the 'Blue Lake' have not been observed to be resistant to pathogens common to *Asters*.

I claim:

1. A new variety of *Aster tataricus* plant substantially as shown and described.

* * * * *